(12) United States Patent
Friend

(10) Patent No.: US 11,504,148 B2
(45) Date of Patent: Nov. 22, 2022

(54) PERSONAL CARE APPLIANCE

(71) Applicant: MICHAEL TODD BEAUTY LP, Port St. Lucie, FL (US)

(72) Inventor: Michael Friend, Port St. Lucie, FL (US)

(73) Assignee: MICHAEL TODD BEAUTY LP, Port St. Lucie, FL (US)

( * ) Notice: Subject to any disclaimer, the term of this patent is extended or adjusted under 35 U.S.C. 154(b) by 288 days.

(21) Appl. No.: 16/508,707

(22) Filed: Jul. 11, 2019

(65) Prior Publication Data

US 2020/0015841 A1 Jan. 16, 2020

Related U.S. Application Data

(60) Provisional application No. 62/696,873, filed on Jul. 12, 2018.

(51) Int. Cl.
| | |
|---|---|
| *A61B 17/32* | (2006.01) |
| *H02J 7/02* | (2016.01) |
| *H02J 7/00* | (2006.01) |
| *H02J 50/12* | (2016.01) |
| *A61B 17/00* | (2006.01) |

(52) U.S. Cl.
CPC .... *A61B 17/320068* (2013.01); *H02J 7/0044* (2013.01); *H02J 7/025* (2013.01); *H02J 50/12* (2016.02); *A61B 2017/00221* (2013.01); *A61B 2017/00398* (2013.01); *A61B 2017/00734* (2013.01); *A61B 2017/00761* (2013.01); *A61B 2017/320004* (2013.01); *A61B 2017/320078* (2017.08); *A61B 2217/007* (2013.01)

(58) Field of Classification Search
CPC ...... A61B 2017/320004; A61B 17/545; A61B 17/320068; A61B 2017/00761; A61B 2017/00398; A61B 2017/00734; A61B 2017/320078; A61B 2217/007; A61B 2217/005; A61B 2017/00221; A61C 17/0208; A61C 17/36; A61C 17/28; A61C 17/224; A61C 17/227; A61C 17/00
USPC .......................................... 606/131
See application file for complete search history.

(56) References Cited

U.S. PATENT DOCUMENTS

| | | |
|---|---|---|
| 6,673,082 B2 | 1/2004 | Mallett et al. |
| 7,318,828 B1 | 1/2008 | Revivo |
| 7,384,405 B2 | 6/2008 | Rhoades |
| 7,572,238 B2 | 8/2009 | Rhoades |

(Continued)

FOREIGN PATENT DOCUMENTS

| | | |
|---|---|---|
| FR | 2845586 | 4/2004 |
| WO | 2005070313 A1 | 8/2005 |

(Continued)

*Primary Examiner* — Katherine H Schwiker
*Assistant Examiner* — Serenity A Miller
(74) *Attorney, Agent, or Firm* — Philip E. Levy; Eckert Seamans Cherin & Mellott, LLC

(57) ABSTRACT

A personal care appliance includes a housing having a first end and a second end located opposite and distal the first end, a treatment head member coupled to the first end of the housing, a sonic motor provided in the housing and being structured to oscillate the head member, and a drainage system comprising a pump provided in the housing, a first conduit fluidly coupled to the pump and the head member, and a second conduit fluidly coupled to the pump and the second end of the housing.

18 Claims, 11 Drawing Sheets

(56) References Cited

U.S. PATENT DOCUMENTS

| | | | |
|---|---|---|---|
| 8,128,638 B2 | 3/2012 | Karasiuk et al. | |
| 8,343,116 B2 | 1/2013 | Ignon et al. | |
| 8,518,001 B2 | 8/2013 | Hasenoehrl et al. | |
| 9,486,615 B2 | 11/2016 | Ignon et al. | |
| 9,750,533 B2 | 9/2017 | Brewer et al. | |
| 9,775,646 B2 | 10/2017 | Shadduck | |
| 2003/0060834 A1* | 3/2003 | Muldner | A61B 17/54 606/131 |
| 2004/0254588 A1 | 12/2004 | Kim | |
| 2007/0293795 A1* | 12/2007 | Carroll | A61B 17/54 601/138 |
| 2011/0040235 A1* | 2/2011 | Castel | A61M 37/00 604/20 |
| 2012/0209294 A1 | 8/2012 | Bitaraf et al. | |
| 2012/0288320 A1* | 11/2012 | Barkhordar | A61C 17/36 401/13 |
| 2013/0158547 A1* | 6/2013 | David | A61B 17/00 606/41 |
| 2014/0352088 A1* | 12/2014 | Wu | A61C 17/34 15/22.1 |
| 2016/0038183 A1 | 2/2016 | Ignon et al. | |
| 2016/0106468 A1 | 4/2016 | Jansen et al. | |
| 2016/0129167 A1* | 5/2016 | Alai | A61M 1/86 604/319 |
| 2016/0324373 A1 | 11/2016 | Planard-Luong | |
| 2016/0331106 A1* | 11/2016 | Khormaei | A46B 11/08 |
| 2017/0036002 A1 | 2/2017 | Ignon et al. | |
| 2017/0266424 A1 | 9/2017 | Ignon et al. | |
| 2017/0360464 A1* | 12/2017 | Jurna | A61B 17/30 |
| 2018/0140329 A1* | 5/2018 | Beijens | A61B 17/545 |

FOREIGN PATENT DOCUMENTS

| | | |
|---|---|---|
| WO | 2007147731 A2 | 12/2007 |
| WO | 2014118596 A1 | 8/2014 |

\* cited by examiner

PERSONAL CARE APPLIANCE

CROSS-REFERENCE TO RELATED APPLICATIONS

This patent application claims the priority benefit under 35 U.S.C. § 119(e) of U.S. Provisional Application No. 62/696,873 filed on Jul. 12, 2018, the contents of which are herein incorporated by reference.

BACKGROUND OF THE INVENTION

1. Field of the Invention

The present invention pertains to personal care appliances, such as a microdermabrasion skin rejuvenating system, that are used to care for, clean and otherwise treat skin.

2. Description of the Related Art

Handheld personal care appliances used to care for, clean or otherwise treat the skin or hair are known and have gained increasing popularity. Such devices are most often used to provide daily hygienic skin care, in particular care for the facial skin. One such personal care appliance is a microdermabrasion skin rejuvenating system. These systems often include roughened head members that are configured to brush against the skin of a patient and cause the skin to be treated. For example, dead skin cells may be relatively easily sloughed away. As a result, this improves the appearance of fine lines, wrinkles, and sun damage. Additionally, these systems also include misting systems that provide a mechanism to apply a mist (e.g., of toner, water, and/or scented water) to the skin of the patient and calm the skin. Furthermore, these systems may also include dry vacuum systems to remove the dead skin cells.

While these systems are known, there is room for improvement in the field of personal care appliances such as microdermabrasion skin rejuvenating systems.

SUMMARY OF THE INVENTION

In one embodiment, an improved personal care appliance includes a housing having a first end and a second end located opposite and distal the first end, a treatment head member coupled to the first end of the housing, a sonic motor provided in the housing and being structured to oscillate the head member, and a drainage system comprising a pump provided in the housing, a first conduit fluidly coupled to the pump and the head member, and a second conduit fluidly coupled to the pump and the second end of the housing.

DETAILED DESCRIPTION OF EXEMPLARY EMBODIMENTS

Figure 1:
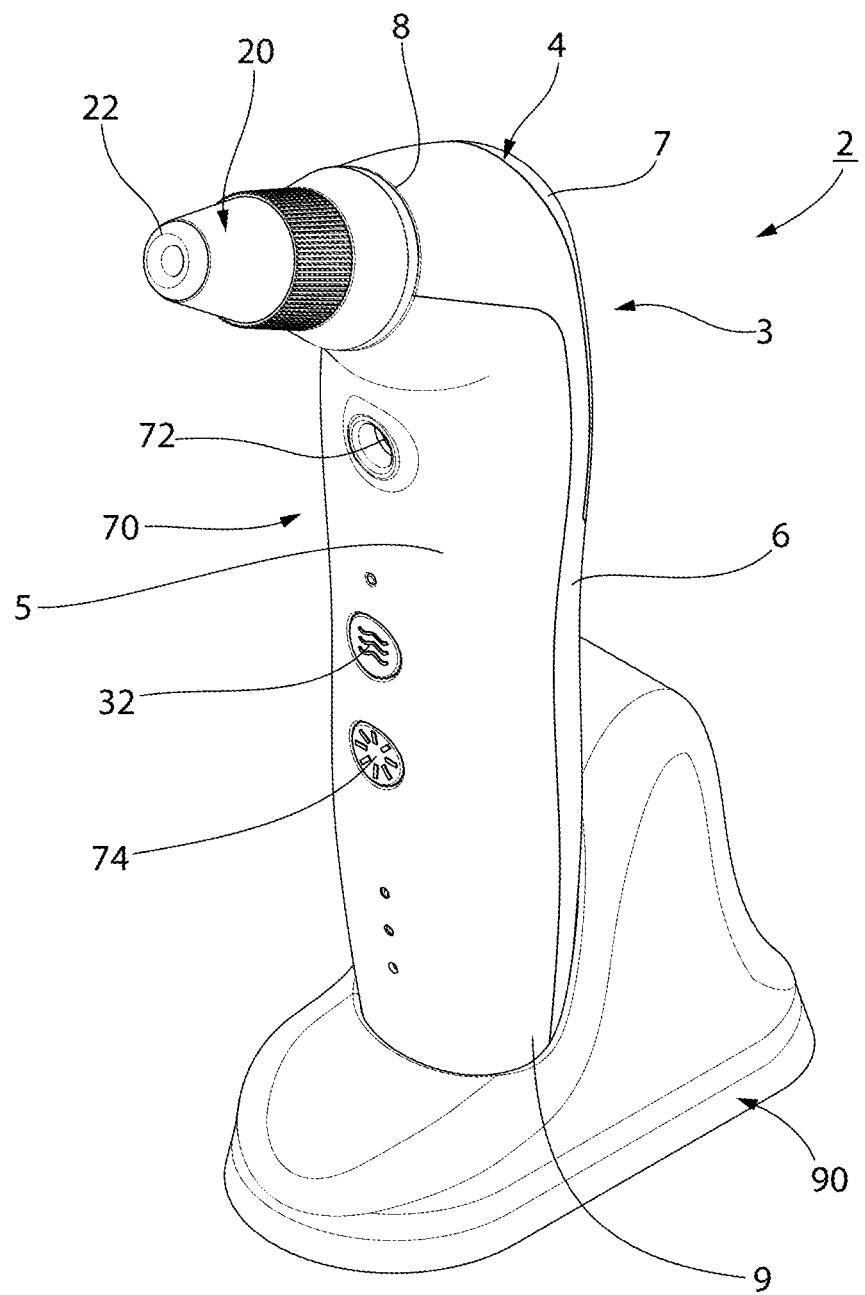
FIG. 1 is a front isometric view of a personal care appliance system, in accordance with one non-limiting embodiment of the disclosed concept.

As used herein, the singular form of "a", "an", and "the" include plural references unless the context clearly dictates otherwise.

As used herein, the statement that two or more parts or elements are "coupled" shall mean that the parts are joined or operate together either directly or indirectly, i.e., through one or more intermediate parts or elements, so long as a link occurs.

As used herein, "directly coupled" means that two elements are directly in contact with each other.

As used herein, "fixedly coupled" or "fixed" means that two elements are coupled so as to move as one while maintaining a constant orientation relative to each other.

As used herein, the word "unitary" means a part is created as a single piece or unit. That is, a part that includes pieces that are created separately and then coupled together as a unit is not a "unitary" part or body.

As used herein, the term "sonic" shall mean speeds of 20 to 20,000 cycles/second.

As employed herein, the statement that two or more parts or elements "engage" one another shall mean that the parts exert a force against one another either directly or through one or more intermediate parts or elements.

As used herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Example 1

FIGS. 1, 1A, 2, and 2A are front (1 and 1A) and rear (2 and 2A) isometric views of a personal care appliance system 2, which is a microdermabrasion skin rejuvenating system used to treat and/or rejuvenate the skin of a user, in accordance with one non-limiting embodiment of the disclosed concept. The personal care appliance system 2 includes a personal care appliance 3 in the form of a microdermabrasion device and, in one example embodiment, a wireless charging station 90 configured to engage and charge the personal care appliance 3, as will be discussed below. Furthermore, as will be discussed below, a user may engage the personal care appliance 3 with their skin in order to polish and smooth the skin for a radiant and youthful look.

Figure 1A:
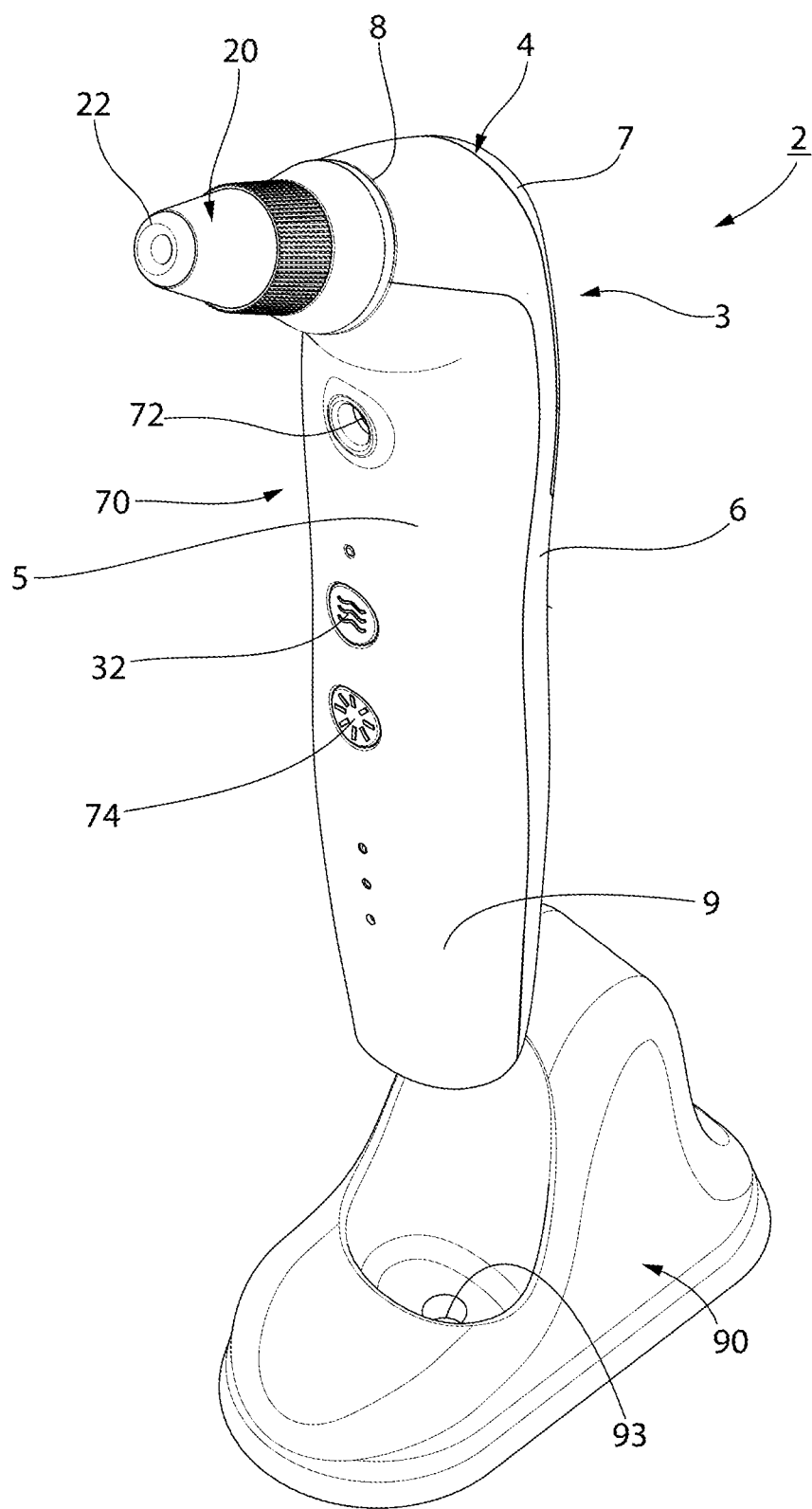
FIG. 1A is an exploded isometric view of the personal care appliance system of FIG. 1.
Figure 2:
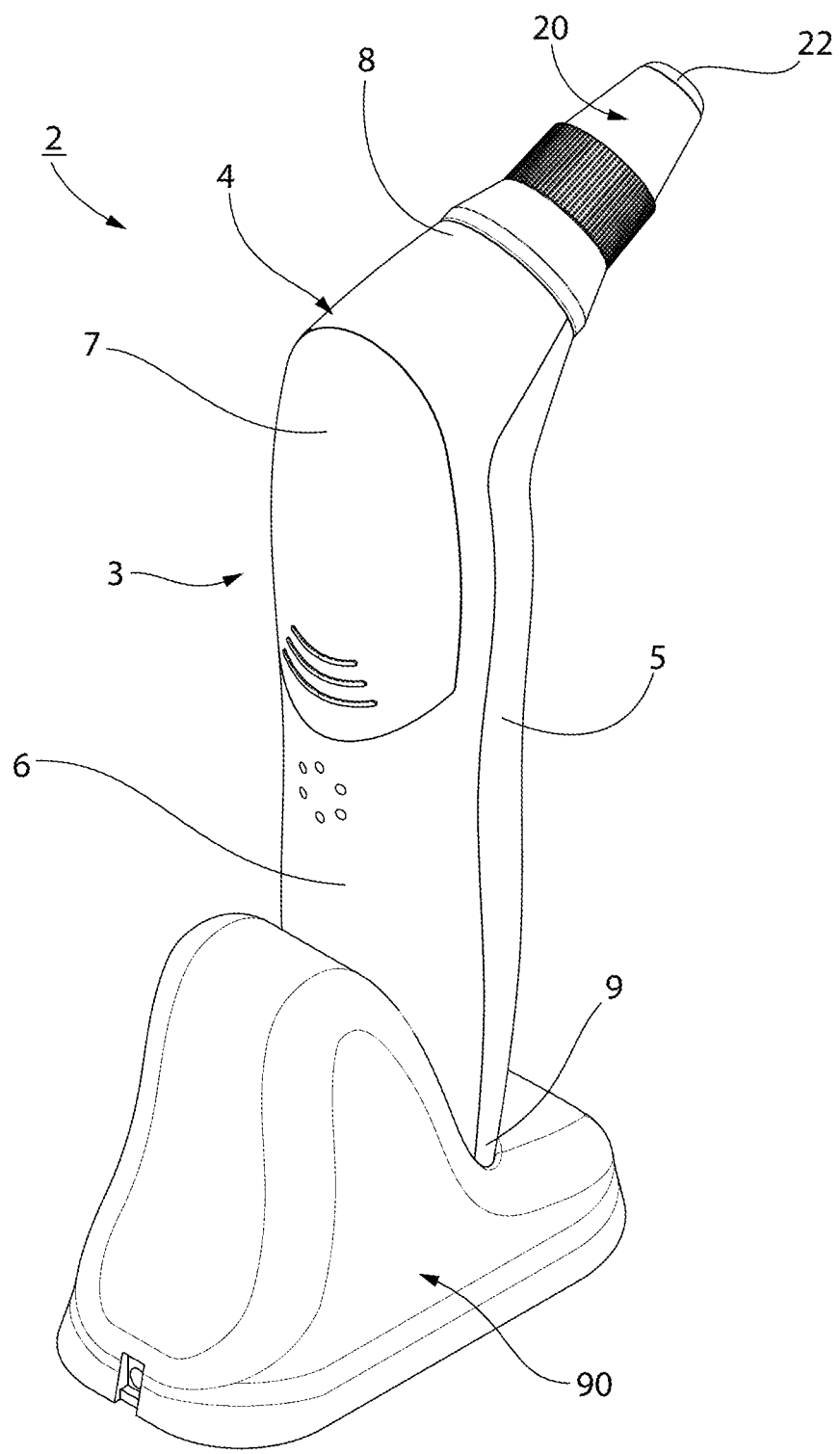
FIG. 2 is a rear isometric view of the personal care appliance system of FIG. 1.

As shown in FIGS. 1, 1A, and 2, the personal care appliance 3 includes a three-part housing 4 and a treatment head member 20 coupled to the housing 4. The housing 4 preferably has a first (front) portion 5, a second (rear) portion 6 coupled to the first portion 5, and a third (also rear) portion 7 coupled to the first and second portions 5,6. The treatment head member 20 has an engaging portion 22 configured to engage and treat the skin of a user. In one example embodiment, the engaging portion 22 is made at least partially of diamond particles in order to treat particularly rough skin of the user. It will, however, be appreciated that suitable alternative treatment head members may be employed, without departing from the scope of the disclosed concept.

Figure 3:
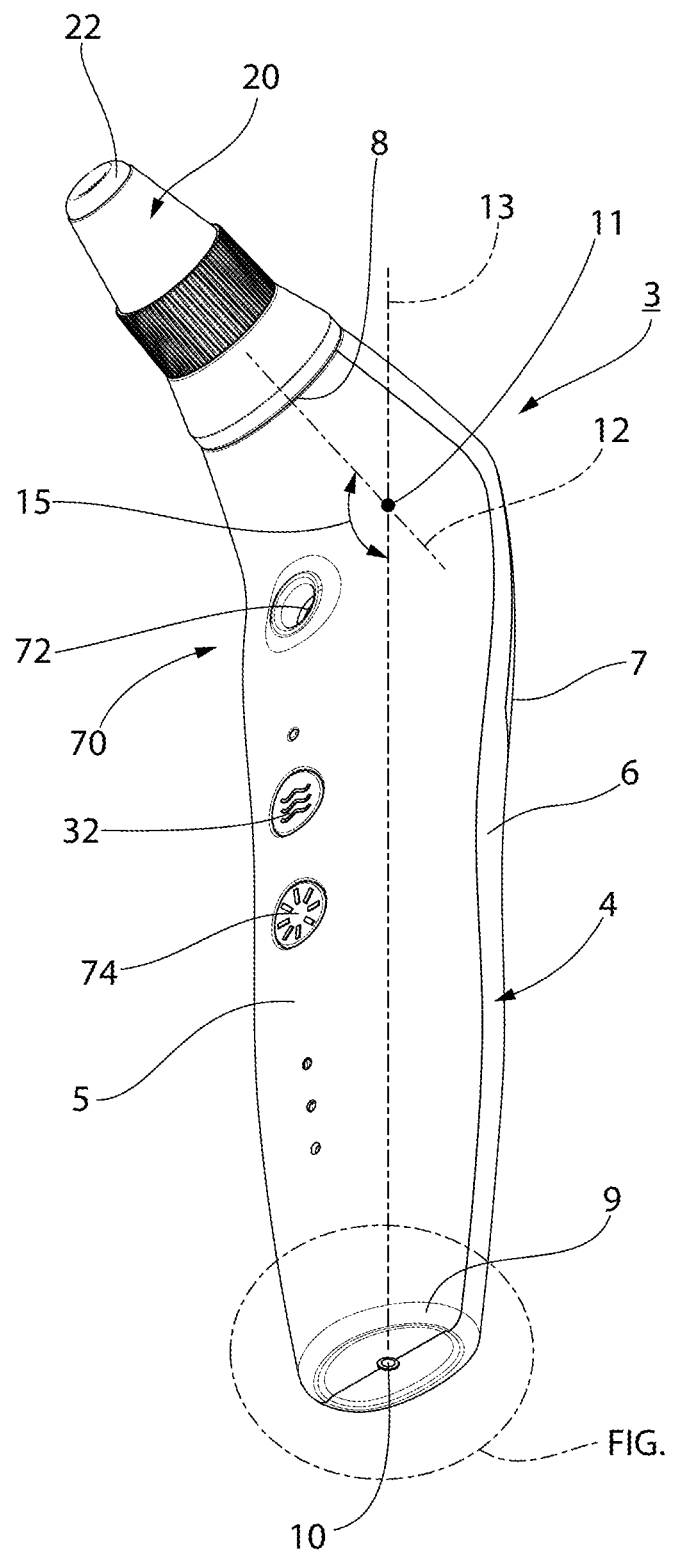
FIG. 3 is a front isometric view of a personal care appliance for the personal care appliance system of FIG. 1.
Figure 4:
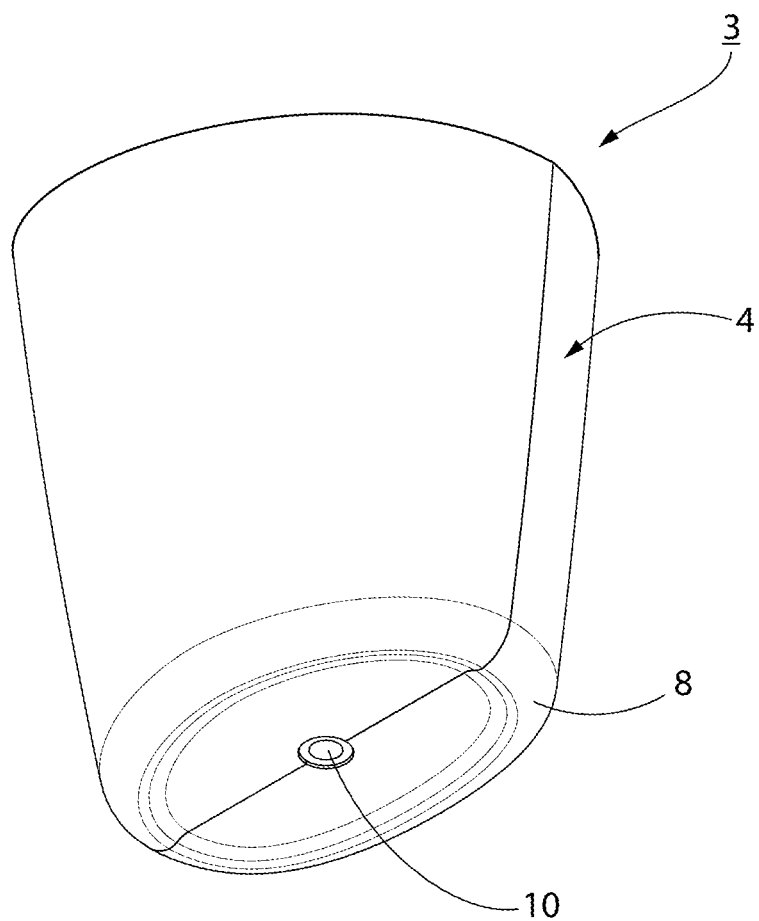
FIG. 4 is an enlarged view of a portion of the personal care appliance of FIG. 3.

FIGS. 3 and 4 show isometric and enlarged isometric views, respectively, of the personal care appliance 3 of the personal care appliance system 2 (FIGS. 1 and 2). Referring to FIG. 3, the housing 4 further has a first end 8 and a second end 9 located opposite and distal the first end 8. As shown more clearly in FIG. 4, the second end 9 of the housing 4 has a thru hole 10. The thru hole 10 provides a fluid pathway from an interior (e.g., a conduit 46, FIG. 5) of the personal care appliance 3 to an exterior thereof, as will be discussed below.

Figure 5:
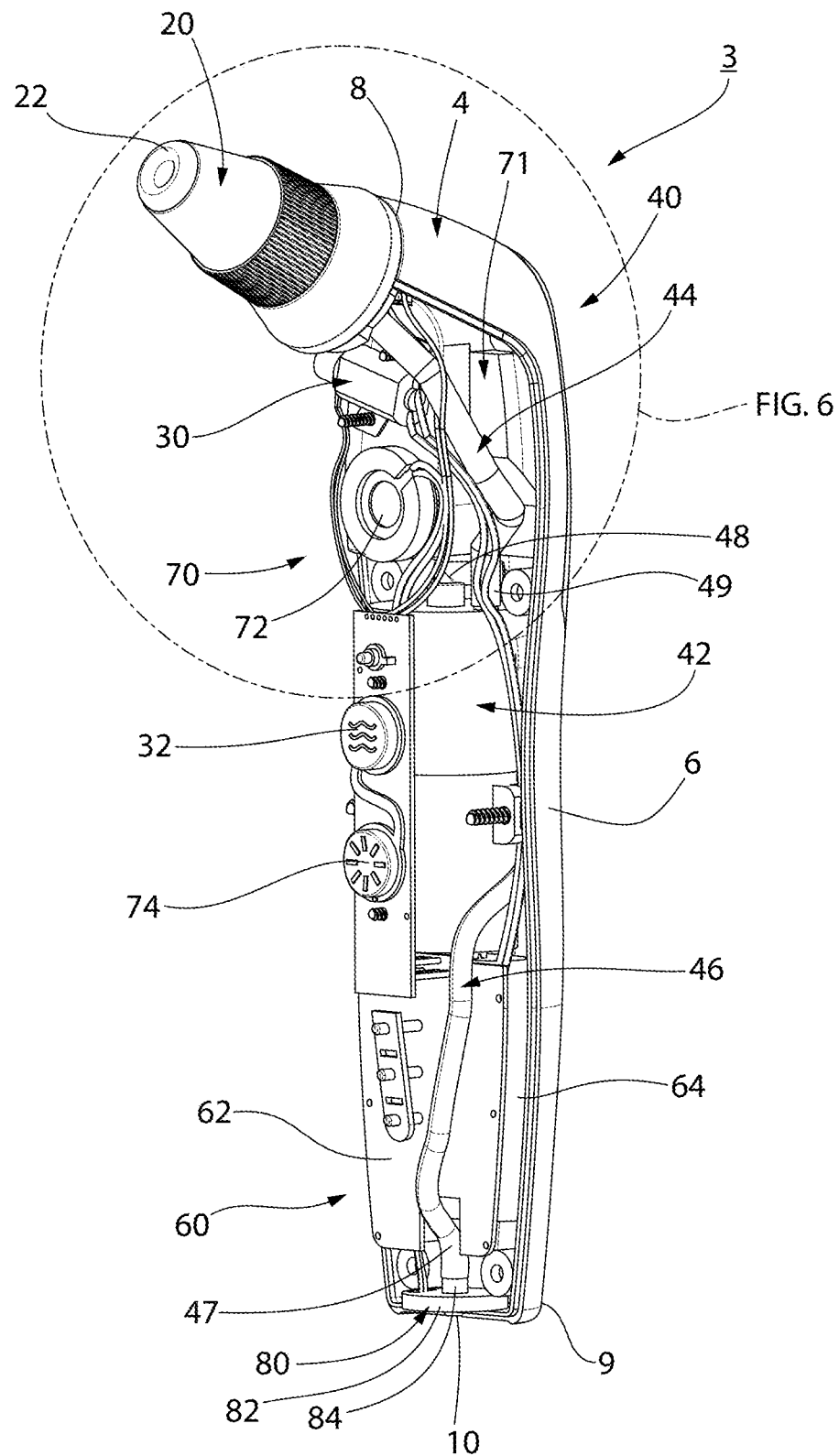
FIG. 5 is a front isometric view of the personal care appliance of FIG. 3, and shown with a portion of the housing removed in order to see hidden features.
Figure 6:
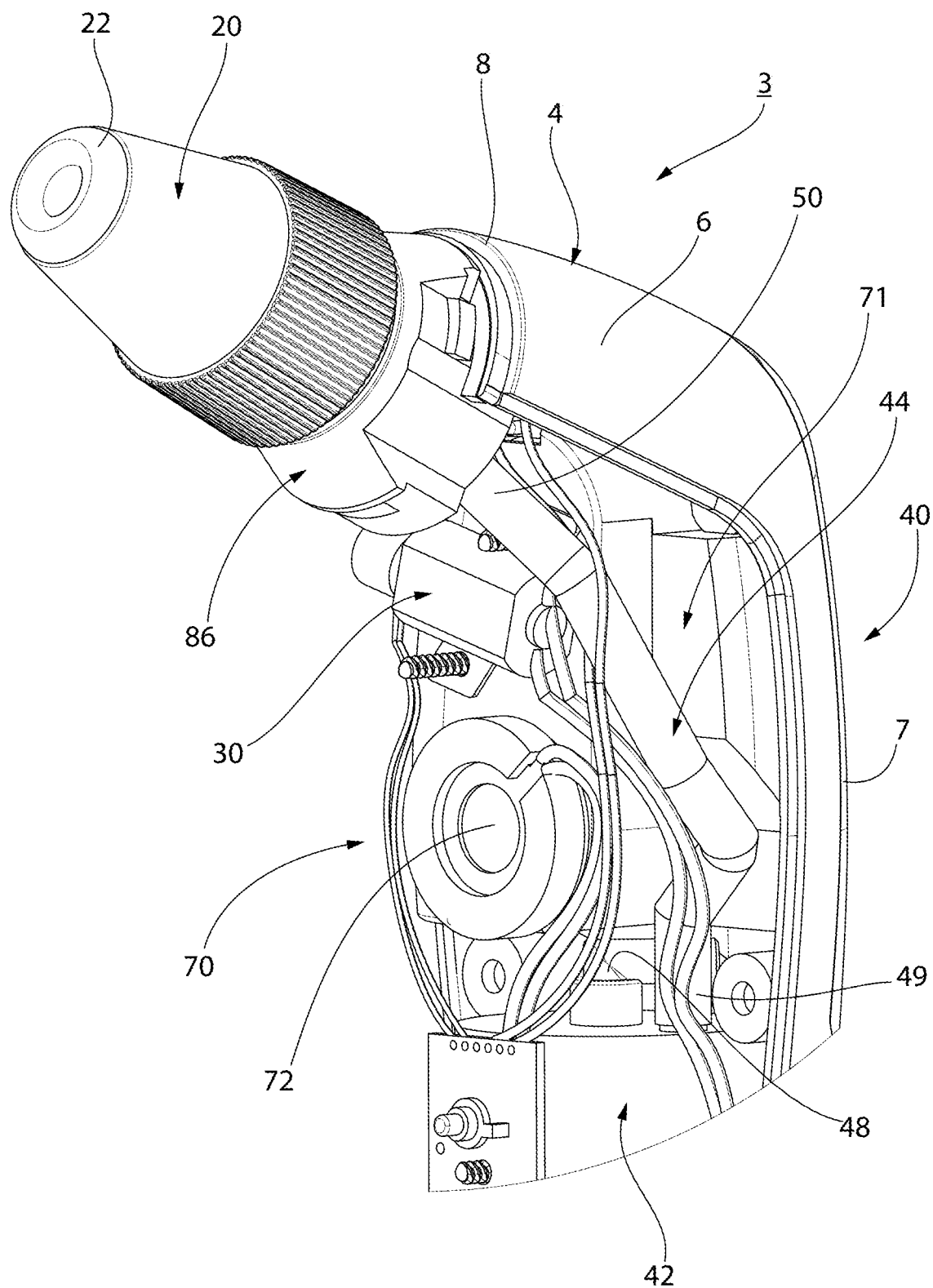
FIG. 6 is an enlarged view of a portion of the personal care appliance of FIG. 5.

FIGS. 5 and 6 show isometric and enlarged isometric views, respectively, of another portion of the personal care appliance 3 of the personal care appliance system 2 (FIGS. 1 and 2). As shown in FIG. 5, the personal care appliance 3 further includes a misting system 70 coupled to the housing 4. The misting system 70 is configured to generate a stream of mist responsive to actuation by a user. The mist may serve several functions. For example and without limitation, the mist from the misting system 70 may be used to soothe skin and close pores. Regarding structure, the misting system 70 preferably includes a liquid reservoir 71 coupled to the housing 4, and a port apparatus 72 fluidly coupled to the reservoir 71. It will be appreciated that the third portion 7 of the housing 4 functions to enclose the liquid reservoir within the housing 4. Furthermore, the misting system 70 has an actuation member 74 electrically connected to the port apparatus 72. As such, upon depression of the actuation member 74 by a user, an electrical signal is sent to the port apparatus 72, thereby allowing liquid from the reservoir 71 to be ejected through the port apparatus 72 in the form of a mist. Furthermore, it will be appreciated herein that the misting system 70 may be structured to generate micromist, and in one example embodiment, a mist of toner, water, and/or scented water. The misting system 70 may generate the micromist by employing a micronizing mechanism/pump that breaks up molecules of the solution (e.g., the toner, water, and/or scented water) into very fine particles.

In accordance with the disclosed concept, the personal care appliance 3 further includes an electronic motor (e.g., without limitation, sonic motor 30) and a drainage system 40 which together allow the personal care appliance 3 to better treat the skin of the user. The sonic motor 30 is coupled to and provided in the housing 4, and is structured to oscillate the personal care appliance 3, and thus the head member 20. In one example embodiment, the sonic motor 30 oscillates the head member 20 at a frequency greater than 200 cycles/second. The sonic motor 30 may optionally be coupled to the housing 4 such that no further components (e.g., no shafts extending from sonic motor 30) are required to cause oscillation of the head member 20. As a result, it will be appreciated that in one example embodiment the sonic motor 30 does not cause rotation of the head member 20, but rather oscillates or vibrates the head member 20. The sonic motor 30 may be actuated by, for example and without limitation, an actuation member 32 which is electrically connected to the sonic motor 30. As will be appreciated, when the sonic motor 30 is operating, after starting from an initial midpoint, the engaging portion 22 of the head member 20 will move back and forth between a first lateral (e.g. left) maximum position and an opposite second lateral (e.g. right) maximum position.

The drainage system 40 preferably includes a pump (e.g., without limitation, wet-dry pump 42) coupled to and provided in the housing 4 and being separate and distinct from the sonic motor 30. In one embodiment, the pump 42 is encapsulated (e.g., enclosed and/or located entirely internal) by the housing 4. The drainage system 40 also includes a first conduit 44 fluidly coupled to the pump 42 and the head member 20, and a second conduit 46 fluidly coupled to the pump 42 and the second end 9 of the housing 4. As shown, in FIG. 5, the second conduit 46 has a first distal portion 47 and a second distal portion 48 located opposite and distal the first distal portion 47. The second distal portion 48 is fluidly coupled to the pump 42, and the first distal portion 47 is located internal with respect to the housing 4, but proximate the thru hole 10 in order to provide a fluid pathway from the pump 42 to an exterior of the personal care appliance 2 (FIGS. 1 and 2). Referring to FIG. 6, the personal care appliance 3 further includes a tubular shaped coupling member 86 coupled to each of the head member 20 and the first end 8 of the housing. Furthermore, the first conduit 44 has a first distal portion 49 and a second distal portion 50 located opposite and distal the first distal portion 49. The second distal portion 50 of the first conduit 44 terminates at and is fluidly coupled to the coupling member 86.

It will be appreciated that the sonic motor 30 and the novel drainage system 40 are advantageous for a number of reasons. For example, when the personal care appliance 3 is being used, liquids and/or solid/liquid mixtures (e.g., misting liquid and dead skin cells) are able to be pulled through the head member 20, pump 42, and conduits 44,46 in a relatively efficient manner while protecting the skin of the user. More specifically, if a user desires to actuate the misting system 70 such that liquid is ejected onto the face of the user, the drainage system 40 allows that liquid, once it has treated the face of the user, and any dead skin cells or other material, to be removed from the face of the user and pulled through the personal care appliance 3 to an exterior thereof, without damaging any of the internal components of the personal care appliance 3.

Referring to FIG. 5, while the misting system 70 is ejecting mist, the pump 42 may simultaneously be pulling a solution (e.g., of mist from the nesting system 70 combined with particulates from the skin of the user) through the first conduit 44. Additionally, because the pump 42 is preferably a wet-dry pump, as opposed to other types of pumps (e.g., dry only pumps not shown) used in many prior art devices (not shown), the solution will not damage the pump 42. More specifically, the pump 42 preferably functions without a bag or filter, and is structured to pull the solution through the first conduit 44 and into a reservoir in the pump 42. From the reservoir, the solution is preferably pulled out through second conduit 46 until it reaches the first distal portion 47. In one example embodiment, the pump 42 is a motor driven diaphragm pump that has a motor, or other suitable actuator, which drives (e.g., via a piston) a diaphragm (e.g., a flexible membrane located in an interior of the pump 42) in order to both let a solution into the pump 42, and also discharge the solution out of the pump.

As shown in FIG. 5, in one example embodiment, the personal care appliance 3 further includes a wireless charging component housing 80 having a cylindrical-shaped base portion 82 (e.g., which is structured to house a conductor 81, shown in FIG. 2A) and a protrusion 84 extending outwardly from the base portion 82. The base portion 82 is preferably coupled to the second end 9 of the housing 4 of the personal care appliance 3. Furthermore, it will be appreciated that the wireless charging component housing 80 has a thru hole through the protrusion 84 and the base portion 82 (and also through the conductor 81 housed therein). As shown, the first distal portion 47 of the second conduit 46 is coupled to the protrusion 84 in order to provide a fluid pathway from the pump 42 to an exterior of the personal care appliance 2 (FIGS. 1 and 2). In one example embodiment, the first distal portion 47 is coupled to the protrusion 84 by a press-fit mechanism. Accordingly, it will be appreciated that the thru hole of the base portion 82 and protrusion 84 of the wireless charging component housing 80 are aligned with the thru hole 10 of the second end 9 of the housing 4 in order to allow the solution to pass through.

Figure 2A:
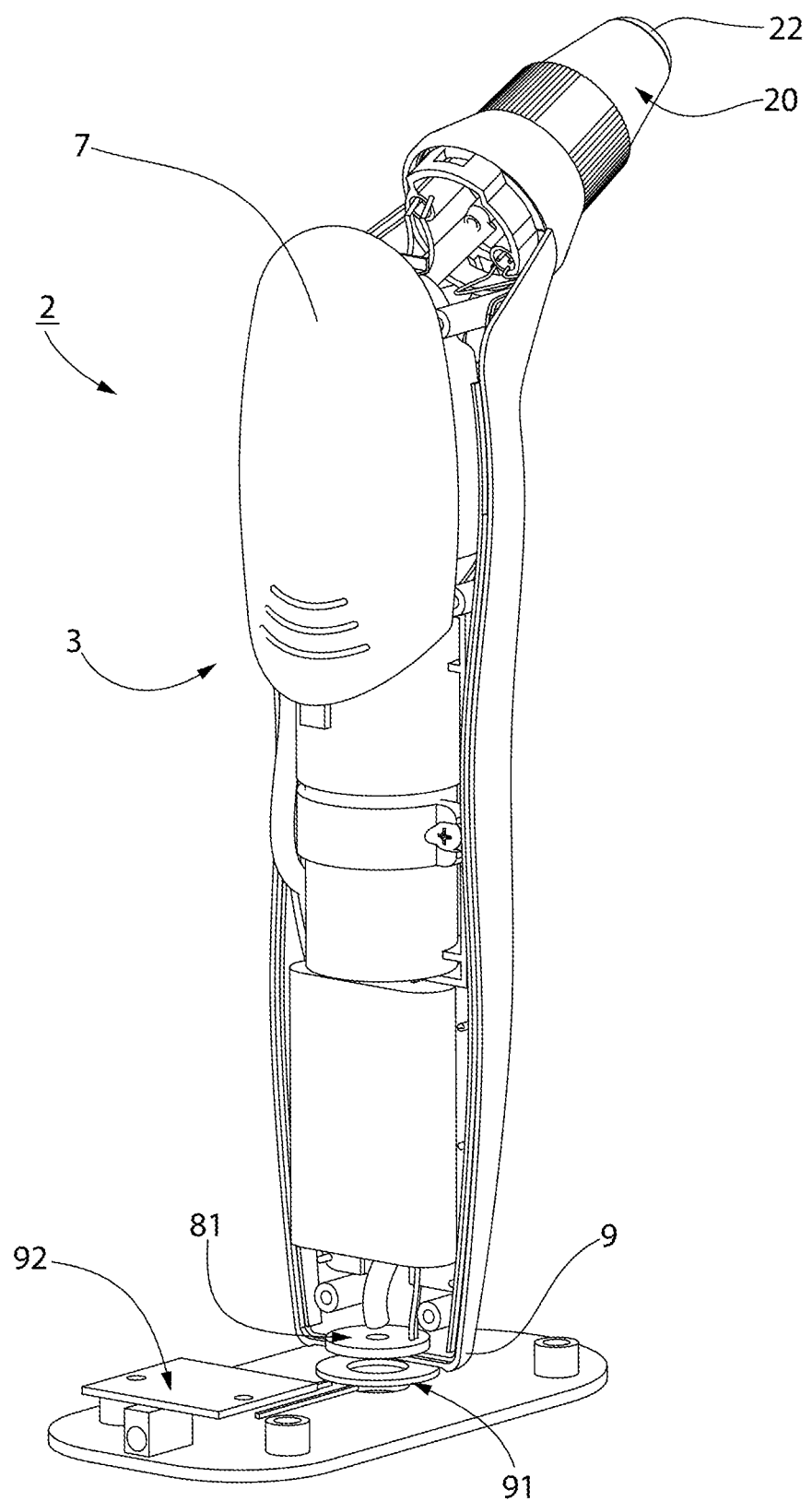
FIG. 2A is another rear isometric view of the personal care appliance system of FIG. 1, shown with portions removed in order to see hidden structures.
Figure 2B:
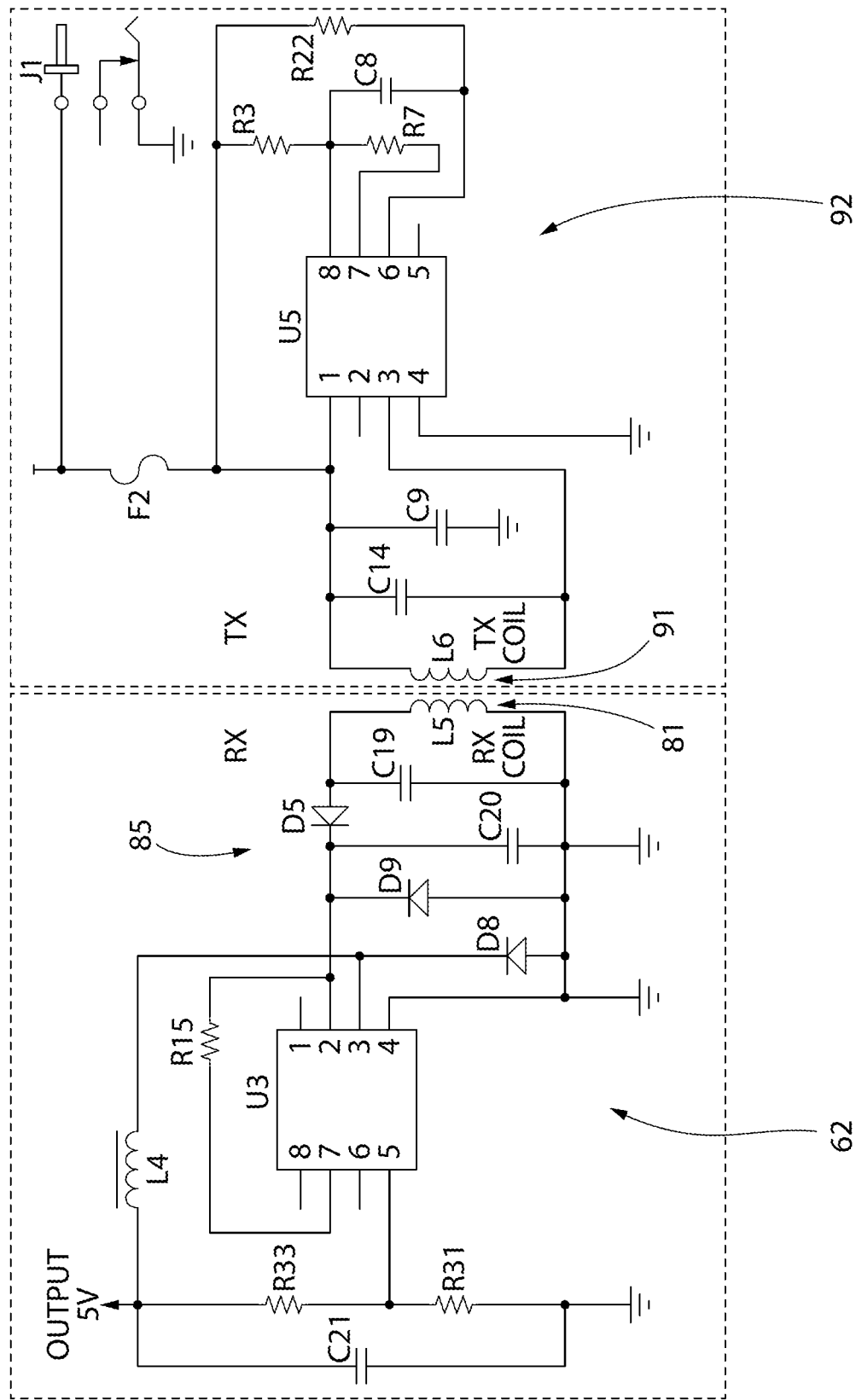
FIG. 2B is a schematic circuitry diagram representing wireless charging of the personal care appliance system of FIG. 1.

The personal care appliance 3 further has a circuitry system 60 coupled to the housing 4. The circuitry system 60 includes a printed circuit board 62, a battery (e.g., without limitation, nickel metal hydride battery 64), and a conductor 81 provided on or housed within base portion 82 and electrically connected to the printed circuit board 62 and the battery 64. In one example embodiment, the conductor 81 is an annular-shaped coiled conductor that functions as an antenna to wirelessly receive, by way of inductive coupling, RF AC energy so that the energy can be used to charge the battery 64. For example, FIG. 2A shows the personal care appliance system 2 with the second portion 6 of the housing 4, the wireless charging component housing 80 (see FIG. 5), and a body portion of the wireless charging station 90 hidden in order to view hidden structures. As shown, the conductor 81 is positioned directly above and in close proximity to a corresponding annular-shaped conductor 91 of the wireless charging station 90. It will be appreciated that the conductor 91 is electrically connected to a printed circuit board 92 (e.g., also structured to be housed within the wireless charging station 90), which is configured to transmit AC power from, for example, an outlet of a wall, to the conductor 91. As such, when power is being transmitted to the conductor 91, the conductor 91 functions as an antenna to wirelessly transmit AC energy to the conductor 81. Referring to FIG. 2B, which is a circuit diagram showing various electrical components provided on and/or coupled to printed circuit board 62 and printed circuit board 92, a rectifier 85 is provided on printed circuit board 62, and is electrically connected to the conductor 81 in order to convert the received AC energy to DC energy, after which the DC electrical energy is passed to the battery 64 to charge the battery. Furthermore, because both of the conductors 81,91 preferably have thru holes (e.g., without limitation, are annular-shaped), and are positioned directly above one another, a pathway is provided through which the solution of water and dead skin cells can exit the personal care appliance system 2.

The battery 64 is preferably electrically connected to the sonic motor 30 and the pump 42 in order to power said components. As shown in FIG. 5, the circuitry system 60 is separate and distinct from the pump 42 and the conduits 44,46. As a result, the pump 42 and the conduits 44,46 preferably define a fluid pathway entirely spaced apart from the circuitry system 60. In other words, fluids (e.g., a solution of mist and skin particles) pulled through the head member 20, pump 42, and conduits 44,46, will preferably not engage with any circuitry in the interior of the personal care appliance 3, thus providing safety to a user and prolonging the life of the personal care appliance 3. In one example embodiment, the wireless charging station 90 (FIGS. 1, 1A, and 2), which engages the second end 9 of the housing 4, preferably has a thru hole 93 aligned with the thru hole 10 of the housing 4 in order to provide a fluid pathway from the first distal end 47 of the second conduit to an exterior of the wireless charging station 90. See, for example, FIG. 1A, depicting the thru hole 93 of the wireless charging station 90. Additionally, it will be appreciated that the thru holes of the conductors 81,91 (FIG. 2A) are likewise so aligned.

As stated above, the sonic motor 30, in addition to the drainage system 40, further functions to better treat the skin of the user. More specifically, it will be appreciated that in prior art personal care devices (not shown), internal pumps function to pull the skin of the user onto and/or into the personal care device. As a result, when users of such devices (not shown) attempt to move the devices across the skin (e.g., of their faces), the devices often do not release from the portions of the skin they are engaged with. This results in skin being pulled and/or stretched, a scenario that is undesirable for anti-aging purposes. The instant disclosed concept, by way of contrast, employs the sonic motor 30 to solve this problem. More precisely, sonic movements proximate the engaging portion 22 of the head member 20 that are generated by the sonic motor 30 advantageously function to release vacuum being pulled by the pump 42. That is, rather than the pump 42 preventing the engaging portion 22 of the head member 20 from sliding and/or moving across the skin of the user, the oscillations of the sonic motor 30 cause a break between the skin and the engaging portion 22 to disturb any such vacuum, thereby allowing the engaging portion 22 to more easily move across the skin of the patient. Accordingly, this movement can be done with minimal and/or without any stretching and/or pulling of the skin. As a result, the personal care appliance 3 of the personal care device 2 provides a novel mechanism to promote anti-aging in the skin of a user.

In addition to the aforementioned benefits provided by the personal care appliance 3, the personal care appliance 3 further has a novel geometry to improve ease of use. Referring to FIG. 3, the housing 3 has a location 11 located proximate the first end 8. The first end 8 and the location 11 form a first axis 12. The second end 9 and the location 11 form a second axis 13. The first axis 12 is preferably located at an angle 15 of between 105 degrees and 145 degrees with respect to the second axis 13, more preferably located at an angle of between 120 degrees and 130 degrees, and most preferably being about 125 degrees. Accordingly, the angle 15 is advantageous in that users can perform treatment on their skin while looking into a mirror, and still be able to see what they are doing, whereas if an angle were about 90 degrees (not shown), a device (not shown) might block such viewing by the user.

Example 2

Figure 7:
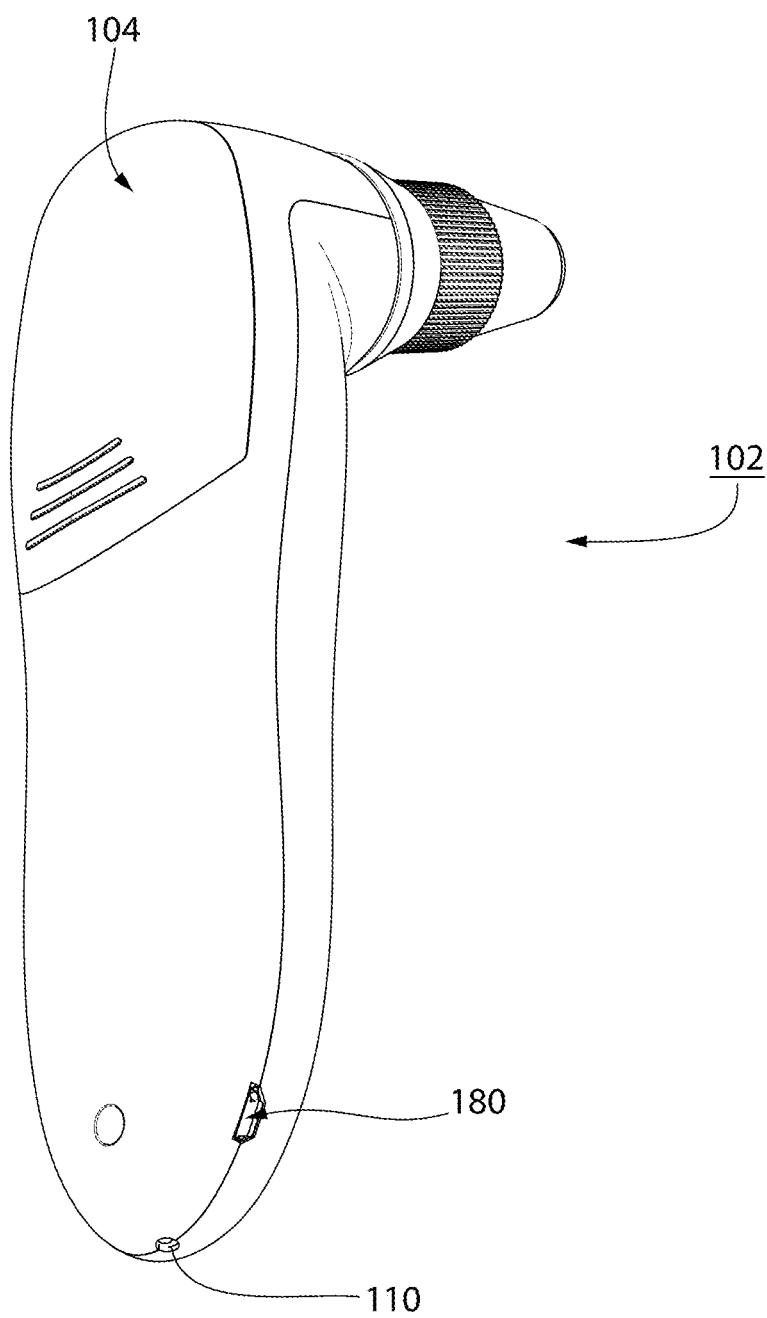
FIG. 7 is a rear isometric view of another personal care appliance, in accordance with another non-limiting embodiment of the disclosed concept.
Figure 8:
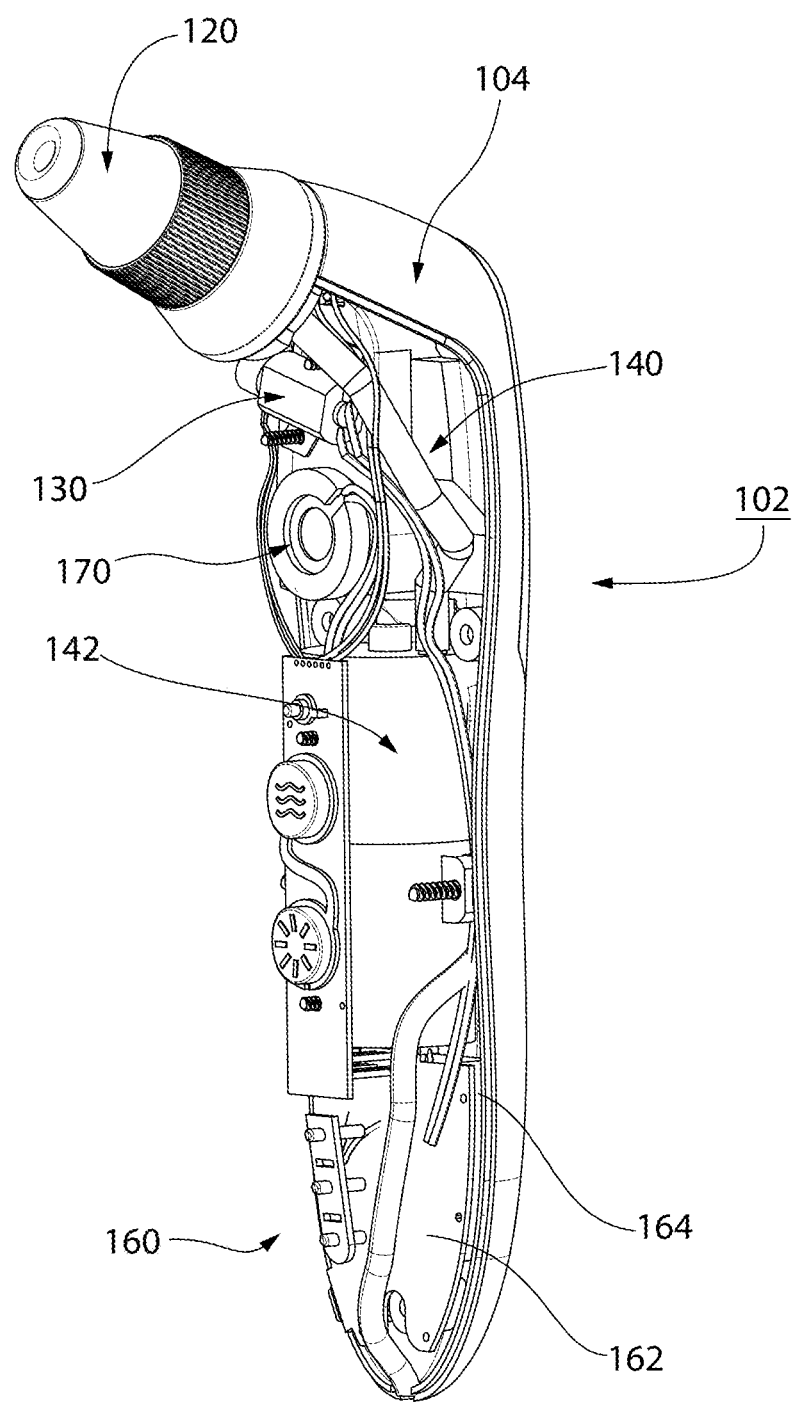
FIG. 8 is a front isometric view of the personal care appliance of FIG. 7, and shown with a portion of the housing removed in order to see hidden features.

FIGS. 7 and 8 show different views of another personal care appliance 102. The personal care appliance 102 is largely the same as the personal care appliance 3, discussed above, except that rather than being charged by way of a separate wireless charging station (e.g., wireless charging station 90), personal care appliance 102 is charged by way of direct wired connection as described below. As shown in FIG. 7, the personal care appliance 102 includes a housing 104 (similar to housing 4 of personal care appliance 3), which has a thru hole 110 in order to allow a solution from the drainage system of the personal care appliance 102 (shown in FIG. 8) to pass therethrough. Personal care appliance 102 further includes a head member 120, a sonic motor 130, a drainage system 140 including a pump 142, and a misting system 170, each structured substantially the same as the head member 20, the sonic motor 30, the drainage system 40 including the pump 42, and the misting system 70, discussed above, and structured to perform the same functions as said components. Referring to FIG. 8, the personal care appliance 102 further includes a circuitry system 160 having a printed circuit board 162 and a lithium battery 164 that is electrically connected to the sonic motor 130 and the pump 142. Furthermore, as shown in FIG. 7, the personal care appliance 102 has a universal serial bus (USB) port 180. It will be appreciated that the USB port 180, unlike the wireless charging component 80 of the personal care appliance 3, provides a mechanism to allow a user to connect a cable to charge and power the lithium battery 164 inside the housing 104.

Accordingly, it will be appreciated that the disclosed concept provides for an improved (e.g., without limitation, better in terms of ability to treat skin, safer, more ergonomic) personal care appliance 3,102. It will also be appreciated that by employing batteries 64,164, whether they be chargeable wirelessly or via a USB port, personal care appliances 3,102 are configured to be self-contained apparatus that do not require wired connections to external devices.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A personal care appliance comprising:
   a housing having a first end and a second end disposed opposite and distal the first end,
   a treatment head member coupled to the first end of said housing,
   a sonic motor provided in said housing and being structured to move said head member at a sonic frequency, and
   a drainage system comprising a pump provided in the housing, wherein the pump is a wet-dry pump, a first conduit fluidly coupled to an input of said pump and said head member, and a second conduit fluidly coupled to an output of said pump and the second end of said housing, said second conduit not being directly connected to said first conduit, wherein a fluid pathway is formed from the head member to the second end of said housing through the first conduit, the pump and the second conduit.

2. The personal care appliance of claim 1 wherein the second end of said housing has a thru hole; and wherein said second conduit has a distal portion disposed proximate the thru hole in order to couple the fluid pathway to an exterior of said personal care appliance.

3. The personal care appliance of claim 2 further comprising a circuitry system provided in said housing; wherein the fluid pathway is spaced apart from said circuitry system.

4. The personal care appliance of claim 3 wherein said circuitry system comprises a rechargeable battery electrically connected to said sonic motor and said pump.

5. The personal care appliance of claim 4 wherein said rechargeable battery is a nickel metal hydride battery or a lithium battery electrically connected to said sonic motor and said pump.

6. The personal care appliance of claim 3 further comprising a misting system provided in said housing and being configured to hold a liquid and generate a stream of mist from the liquid responsive to actuation by a user.

7. The personal care appliance of claim 6 wherein said misting system is structured to generate a micro mist.

8. The personal care appliance of claim 1 wherein said sonic motor is structured to oscillate said head member at a frequency greater than 200 cycles/second.

9. The personal care appliance of claim 1 wherein said head member has an engaging portion configured to engage the skin of a user; and wherein the engaging portion is made at least partially of diamond particles.

10. The personal care appliance of claim 1 wherein said housing further has a location disposed proximate the first end; wherein the first end and the location form a first axis; wherein the second end and the location form a second axis; and wherein the first axis is disposed at an angle of between 105 degrees and 145 degrees with respect to the second axis.

11. The personal care appliance of claim 10 wherein the angle is between 120 degrees and 130 degrees.

12. The personal care appliance of claim 11 wherein the angle is 125 degrees.

13. The personal care appliance of claim 1 further comprising a tubular shaped coupling member coupled to each of said head member and said housing; and wherein said first conduit has a distal portion terminating at and being fluidly coupled to said coupling member.

14. A personal care appliance comprising:
   a housing having a first end and a second end disposed opposite and distal the first end,
   a treatment head member coupled to the first end of said housing,
   a sonic motor provided in said housing and being structured to move said head member at a sonic frequency,
   a drainage system comprising a pump provided in the housing, wherein the pump is a wet-dry pump, a first conduit fluidly coupled to an input of said pump and said head member, and a second conduit fluidly coupled to an output of said pump and the second end of said housing such that a fluid pathway is formed from the head member to the second end of said housing through the first conduit, the pump and the second conduit, wherein the second end of said housing has a thru hole, and wherein said second conduit has a distal portion disposed proximate the thru hole in order to couple the fluid pathway to an exterior of said personal care appliance, a circuitry system provided in said housing, wherein the fluid pathway is spaced apart from said circuitry system, and a wireless charging component housing and a conductor coupled thereto that is structured to receive RF energy; wherein the wireless charging component housing and the conductor are each disposed proximate the second end of the housing; wherein the distal portion of the second conduit is coupled to the wireless charging component housing; and wherein each of the wireless charging component housing and the conductor has a thru hole in order to allow fluid from the distal portion of the second conduit to pass therethrough.

15. A personal care appliance system comprising:
a wireless charging station; and
a personal care appliance structured to be wirelessly charged by the wireless charging station, the personal care appliance comprising:
a housing having a first end and a second end disposed opposite and distal the first end, the second end being structured to engage the wireless charging station,
a treatment head member coupled to the first end of said housing,
a sonic motor provided in said housing and being structured to move said head member at a sonic frequency, and
a drainage system comprising a pump provided in the housing, wherein the pump is a wet-dry pump, a first conduit fluidly coupled to an input of said pump and said head member, and a second conduit fluidly coupled to an output of said pump and the second end of said housing, said second conduit not being directly connected to said first conduit, wherein a fluid pathway is formed from the head member to the second end of said housing through the first conduit, the pump and the second conduit.

16. The personal care appliance system of claim 15 wherein the second end of said housing has a thru hole, wherein said wireless charging station has a second thru hole aligned with the thru hole of said housing in order to couple the fluid pathway from the distal end of said second conduit to an exterior of said wireless charging station.

17. A personal care appliance system comprising:
a wireless charging station; and
a person care appliance structured to be wirelessly charged by the wireless charging station, the personal care appliance comprising:
a housing having a first end and a second end disposed opposite and distal the first end, the second end being structured to engage the wireless charging station,
a treatment head member coupled to the first end of said housing,
a sonic motor provided in said housing and being structured to move said head member at a sonic frequency,
a drainage system comprising a pump provided in the housing, wherein the pump is a wet-dry pump, a first conduit fluidly coupled to an input of said pump and said head member, and a second conduit fluidly coupled to an output of said pump and the second end of said housing such that a fluid pathway is formed from the head member to the second end of said housing through the first conduit, the pump and the second conduit, and
a wireless charging component housing and a conductor housed therein; wherein the wireless charging component housing and the conductor are each disposed proximate the second end of the housing; wherein the distal portion of the second conduit is coupled to the wireless charging component housing; and wherein each of the wireless charging component housing and the conductor has a thru hole in order to allow fluid from the distal portion of the second conduit to pass therethrough.

18. The personal care appliance system of claim 17 wherein said wireless charging station comprises a body portion and a conductor disposed therein; wherein said conductor of said wireless charging station has a thru hole aligned with the thru holes of said wireless charging component housing and said conductor of said personal care appliance in order to allow fluid from the distal portion of the second conduit to pass therethrough.

* * * * *